United States Patent
Stegall et al.

(10) Patent No.: US 10,602,127 B2
(45) Date of Patent: Mar. 24, 2020

(54) 3D IMAGE CAPTURE APPARATUS WITH COVER WINDOW FIDUCIALS FOR CALIBRATION

(71) Applicant: 3M INNOVATIVE PROPERTIES COMPANY, St. Paul, MN (US)

(72) Inventors: David B. Stegall, St. Paul, MN (US); Vladimir Kryzhniy, St. Paul, MN (US); Eric S. Hansen, Arden Hills, MN (US); Aya Eid, St. Paul, MN (US); Shannon D. Scott, Hudson, WI (US); Zhisheng Yun, Woodbury, MN (US); James L. Graham, II, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/654,327

(22) Filed: Oct. 16, 2019

(65) Prior Publication Data

US 2020/0053344 A1   Feb. 13, 2020

Related U.S. Application Data

(63) Continuation of application No. 14/582,255, filed on Dec. 24, 2014, now abandoned.

(51) Int. Cl.
*H04N 5/225* (2006.01)
*H04N 17/00* (2006.01)
(Continued)

(52) U.S. Cl.
CPC ....... *H04N 13/257* (2018.05); *A61B 1/00057* (2013.01); *A61B 1/00096* (2013.01);
(Continued)

(58) Field of Classification Search
CPC ... G02B 27/0075; G02B 27/32; H04N 5/2256
(Continued)

(56) References Cited

U.S. PATENT DOCUMENTS

| 6,437,823 B1 | 8/2002 | Zhang |
| 7,605,817 B2 | 10/2009 | Zhang |

(Continued)

FOREIGN PATENT DOCUMENTS

| JP | 2002125247 | 4/2002 |
| KR | 100150055 | 12/1998 |

(Continued)

OTHER PUBLICATIONS

Z. Zhang, "A Flexible New Technique for Camera Calibration," *IEEE Transactions on Pattern Analysis and Machine* Intelligence, 22(11):1330-1334, 2000.
(Continued)

*Primary Examiner* — Jefferey F Harold
*Assistant Examiner* — Jean W Desir

(57) ABSTRACT

A 3D imaging apparatus with enhanced depth of field to obtain electronic images of an object for use in generating a 3D digital model of the object. The apparatus includes a housing having mirrors positioned to receive an image from an object external to the housing and provide the image to an image sensor. The optical path between the object and the image sensor includes an aperture element having apertures for providing the image along multiple optical channels with a lens positioned within each of the optical channels. The apparatus also includes a transparent cover positioned within the optical path and having a plurality of fiducials. The depth of field of the apparatus includes the cover, allowing the fiducials to be used to calibrate the apparatus or verify and correct the existing calibration of it.

26 Claims, 8 Drawing Sheets

(51) Int. Cl.

| | | |
|---|---|---|
| *H04N 13/257* | (2018.01) | |
| *G02B 27/32* | (2006.01) | |
| *A61B 1/00* | (2006.01) | |
| *A61C 9/00* | (2006.01) | |
| *A61B 1/24* | (2006.01) | |
| *G03B 17/17* | (2006.01) | |
| *H04N 13/236* | (2018.01) | |
| *H04N 13/246* | (2018.01) | |
| *G02B 27/00* | (2006.01) | |

(52) U.S. Cl.
CPC ...... *A61B 1/00172* (2013.01); *A61B 1/00177* (2013.01); *A61B 1/24* (2013.01); *A61C 9/0053* (2013.01); *G02B 27/32* (2013.01); *H04N 5/2252* (2013.01); *H04N 5/2253* (2013.01); *H04N 5/2256* (2013.01); *H04N 17/002* (2013.01); *G02B 27/0075* (2013.01); *G03B 17/17* (2013.01); *H04N 13/236* (2018.05); *H04N 13/246* (2018.05)

(58) Field of Classification Search
USPC ............ 348/49, 50, 54, 46, 77, 66, 61, 180; 356/247, 256
See application file for complete search history.

(56) References Cited

U.S. PATENT DOCUMENTS

| | | | |
|---|---|---|---|
| 7,742,635 B2 | 6/2010 | Rohaly | |
| 7,956,862 B2 | 6/2011 | Zhang | |
| D674,091 S | 1/2013 | Carlson | |
| 8,493,574 B2 | 7/2013 | Hart | |
| 8,619,144 B1 | 12/2013 | Chang | |
| 9,591,286 B2 | 3/2017 | Yun | |
| 9,967,543 B2* | 5/2018 | Yun | A61B 1/00096 |
| 2002/0054384 A1 | 5/2002 | Motamed | |
| 2004/0136002 A1 | 7/2004 | Whaite et al. | |
| 2010/0007718 A1 | 1/2010 | Rohaly, Jr. et al. | |
| 2010/0238279 A1 | 9/2010 | Thorns et al. | |
| 2010/0245541 A1 | 9/2010 | Zhao | |
| 2011/0157373 A1 | 6/2011 | Ye | |
| 2012/0105593 A1 | 5/2012 | Berestov et al. | |
| 2012/0154541 A1 | 6/2012 | Scott | |
| 2013/0141558 A1 | 6/2013 | Jeon et al. | |
| 2013/0235165 A1 | 9/2013 | Gharib et al. | |
| 2017/0127042 A1 | 5/2017 | Yun | |

FOREIGN PATENT DOCUMENTS

| | | |
|---|---|---|
| WO | WO 2007/036457 | 4/2007 |
| WO | WO 2014/068097 | 5/2014 |
| WO | WO 2014/102779 | 7/2014 |

OTHER PUBLICATIONS

Owen et al., "What is the best fiducial?," IEEE International Augmented Reality Toolkit Workshop—ART, 8 pages, 2002.
PCT International Search Report for PCT/US2015/065480, dated Apr. 11, 2016.

* cited by examiner

3D IMAGE CAPTURE APPARATUS WITH COVER WINDOW FIDUCIALS FOR CALIBRATION

BACKGROUND

Three-dimensional (3D) image scanners are typically calibrated after assembly. The calibration process permits the scanners to produce accurate 3D measurements of solid objects placed in the field of view of the system. In addition, the calibration process characterizes the thermal sensitivity of the scanner during operation and removes the thermal-dependent error from 3D measurements. As the scanner ages over the long-term, there is the possibility that the physical state of the scanner can drift from the originally calibrated state. The drifted state can cause small but measurable errors in the 3D measurements of solid objects. A field calibration target can be used to correct a more severe aging-related drift from the initial calibration. However, the field target calibration requires active participation by the user of the scanner, which can be inconvenient and not necessarily used when needed to recalibrate the scanner.

SUMMARY

A first 3D imaging apparatus, consistent with the present invention, includes a housing and an image sensor within the housing. First and second mirrors are positioned to receive an image from an object external to the housing and provide the image to the image sensor. An aperture element having a plurality of apertures is located along an optical path between the object and the image sensor for providing the image along a plurality of optical channels to the image sensor. The apparatus also includes a transparent cover positioned within the optical path and having a plurality of fiducials. The depth of field of the apparatus includes the transparent cover along with the fiducials.

A second 3D imaging apparatus, consistent with the present invention, includes a housing and an image sensor within the housing. A mirror is positioned to receive an image from an object external to the housing and provide the image to the image sensor. An aperture element having a plurality of apertures is located along an optical path between the object and the image sensor for providing the image along a plurality of optical channels to the image sensor. The apparatus also includes a transparent cover positioned within the optical path and having a plurality of fiducials. The depth of field of the apparatus includes the transparent cover along with the fiducials.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Embodiments include using fiducials on a cover window of a 3D scanner for use in calibrating the scanner or checking the calibrated state of the scanner. An example of a 3D scanner having a cover window within its depth of field is disclosed in U.S. patent application Ser. No. 14/277,113, entitled "3D Image Capture Apparatus with Depth of Field Extension," and filed May 14, 2014, which is incorporated herein by reference as if fully set forth. Systems to generate 3D images or models based upon image sets from multiple views are disclosed in U.S. Pat. Nos. 7,956,862 and 7,605,817, both of which are incorporated herein by reference as if fully set forth. These systems can be included in a housing providing for hand-held use, and an example of such a housing is disclosed in U.S. Pat. No. D674,091, which is incorporated herein by reference as if fully set forth.

3D Image Capture Apparatus

Figure 1:
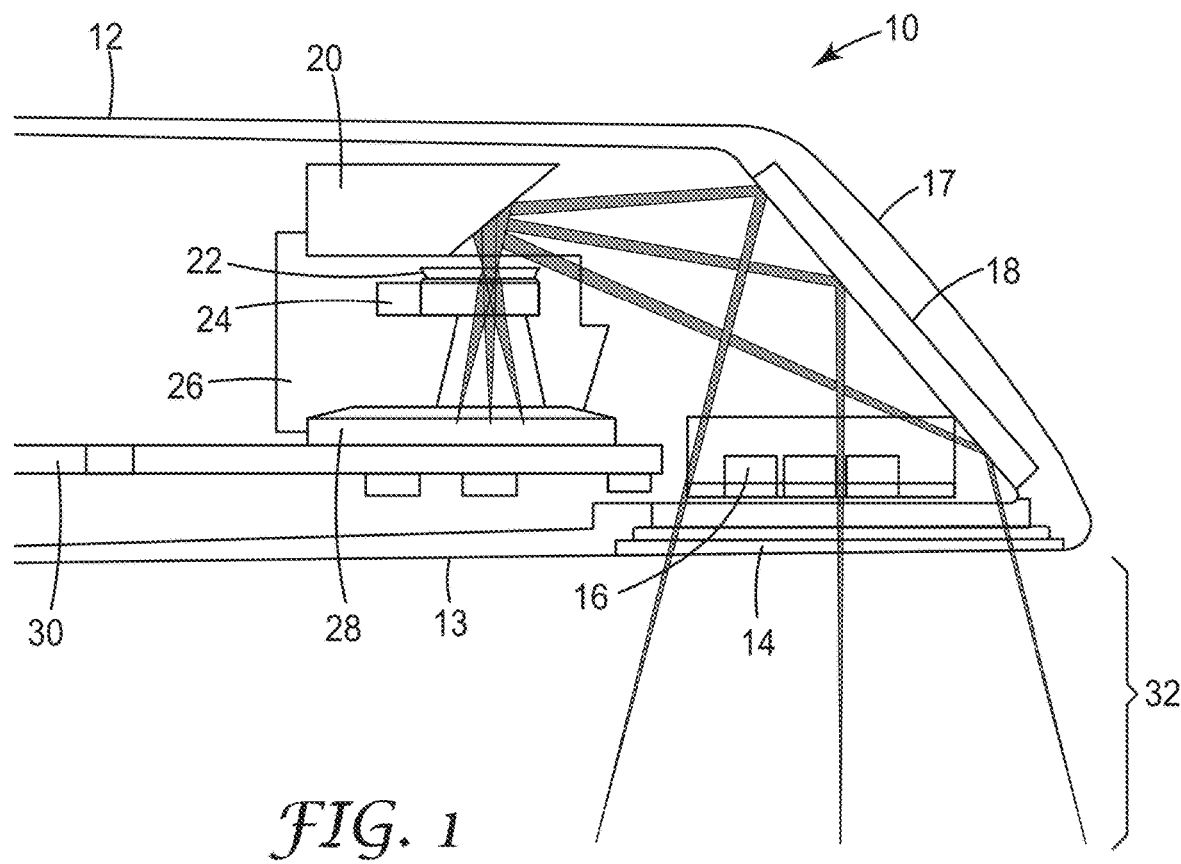
FIG. 1 is a side view of a 3D imager with depth of field extension.

FIG. 1 is a side view of a 3D imager 10 with depth of field extension through the use of two mirrors. System 10 includes a housing 12, mirrors 18 and 20, an aperture element 22, lenses 24, and an image sensor 28. Housing 12 has an angled tip 17 with mirror 18 secured adjacent an interior surface of the tip. A mechanical holder 26 is used to hold mirror 20, aperture element 22, and lenses 24 in position over image sensor 28. A circuit board 30 can receive electronic signals from image sensor 28 representing the images and transmit the signals for further processing to generate a 3D model of the object. Housing 12 includes a transparent cover 14 and light sources 16 adjacent the cover to illuminate an object to be imaged. In this design, image sensor 28 is positioned substantially parallel to an object plane of the object. The imager has a depth of field 32 which includes housing 12, in particular a bottom surface 13 of the housing. The depth of field can alternatively include and extend into the inside of housing 12. By having the depth of field include the housing, imager 10 can be placed directly on (in physical contact with) an object to be imaged, such as on teeth for intra-oral scanning.

Figure 2:
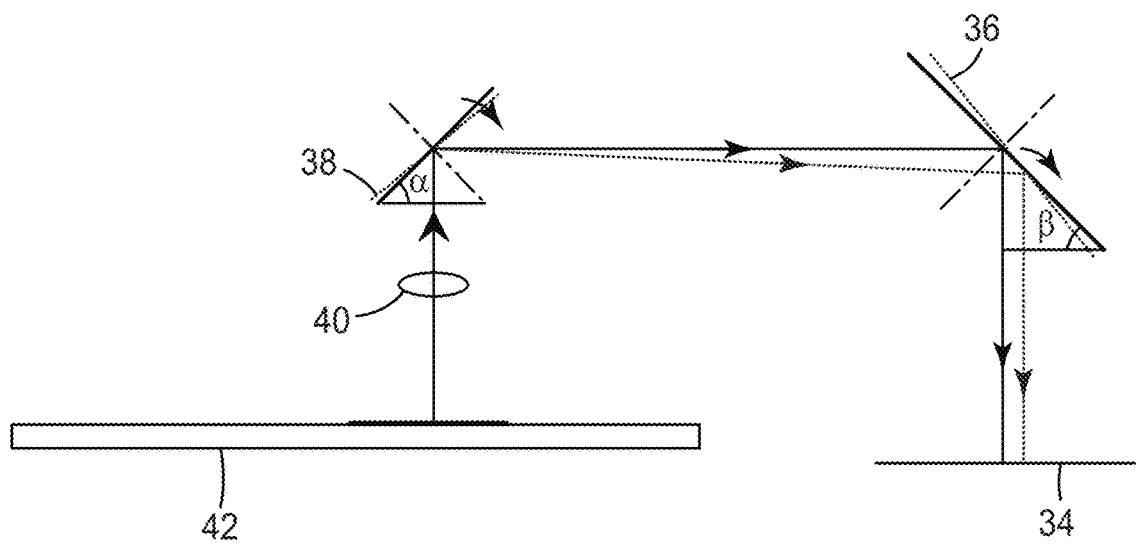
FIG. 2 is a diagram illustrating use of two fold mirrors for depth of field extension.

For the configuration of imager 10 of FIG. 1, the image plane (image sensor surface plane) 42 is positioned along the horizontal plane with object plane 34, as shown in FIG. 2. Mirrors 36 and 38 provide an image of an object at object plane 34 through a lens 40 to an image sensor at image plane 42. If the image sensor surface is normal to the optical axis of lens 40, to achieve good image quality over the entire field of view of object plane 34, object plane 34 needs to be parallel to image plane 42. If $\alpha$ is the angle of mirror 38 to image plane 42 and $\beta$ is the angle of the mirror 36 to object plane 34, to have a good image quality over the lens field of view, mirrors 36 and 38 have the following relationship: $\alpha+\beta=90°$.

FIGS. 1 and 2 show a configuration using two planar fold mirrors. For the two fold mirrors configuration, either of the two fold mirrors, or both of the mirrors, can be implemented with concave mirrors. If concave mirrors are used, the position of the image sensor can be adjusted to compensate for the focus of the concave mirror and obtain sharp images.

Figure 3:
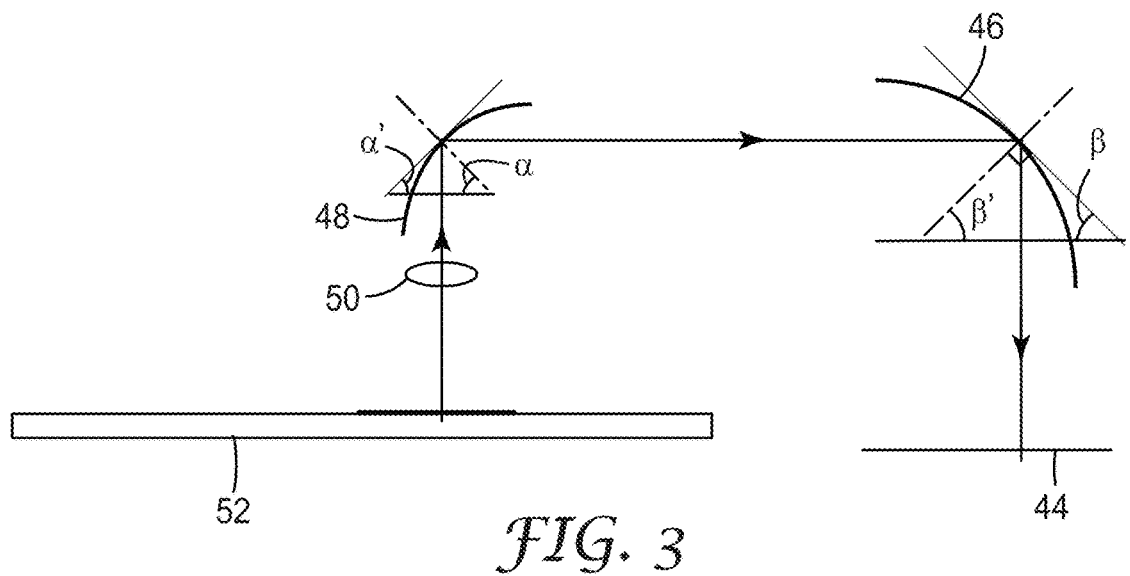
FIG. 3 is a diagram illustrating use of two concave mirrors for depth of field extension.

FIG. 3 illustrates a system using two concave mirrors. Mirrors 46 and 48 provide an image of an object at object plane 44 through a lens 50 to an image sensor at image plane 52. If the image sensor surface is normal to the optical axis of lens 50, to achieve good image quality over the entire field of view of object plane 44, object plane 44 needs to be parallel to image plane 52. If $\alpha'$ is the angle of mirror 48 to image plane 52 and $\beta'$ is the angle of the mirror 46 to object plane 44, to have a good image quality over the lens field of view, mirrors 46 and 48 have the following relationship: $\alpha'+\beta'=90°$.

Figure 4:
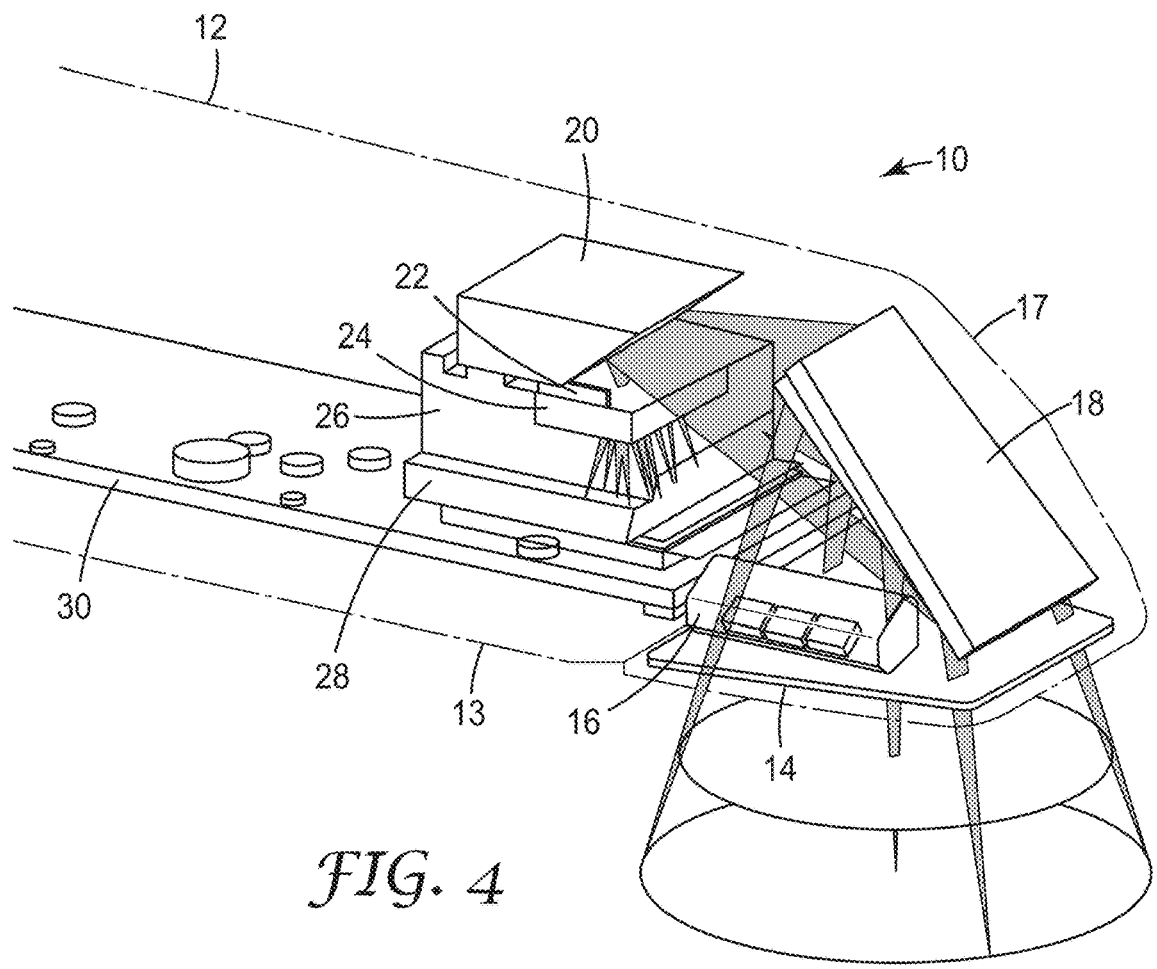
FIG. 4 is a perspective view of the 3D imager of FIG. 1.
Figure 5:
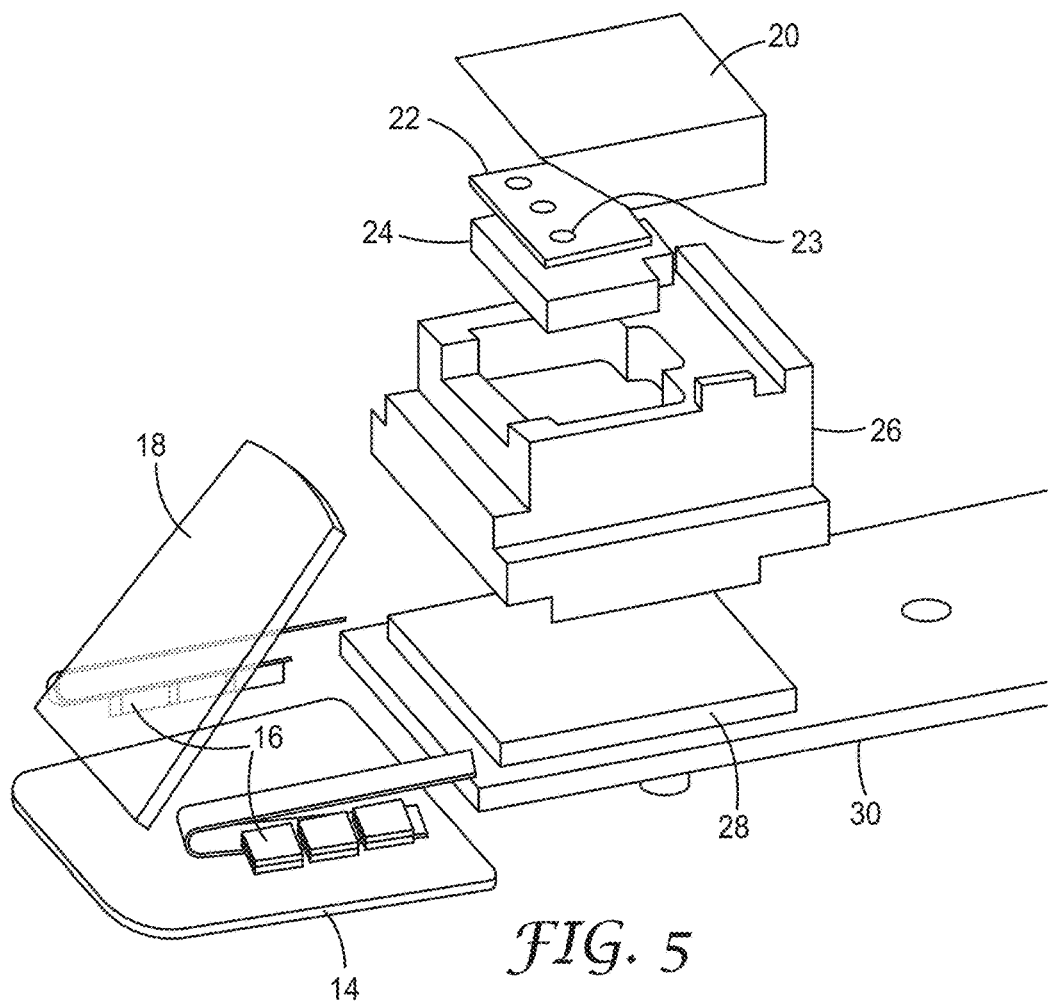
FIG. 5 is an exploded perspective view of the 3D imager of FIG. 1.
Figure 6:
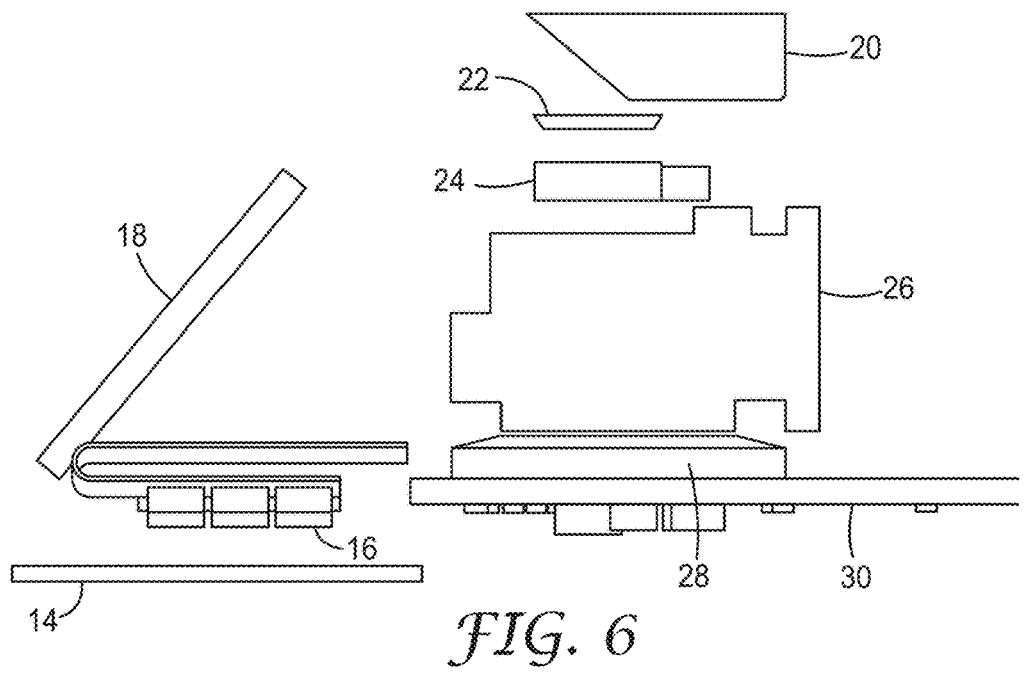
FIG. 6 is an exploded side view of the 3D imager of FIG. 1.

FIGS. 4-6 are perspective, exploded perspective, and exploded side views, respectively, of 3D imager 10 of FIG. 1. FIG. 5 illustrates apertures 23 in aperture element 22 to create multiple channels. Although three apertures are shown, aperture element 22 can alternatively have two apertures for a two channel system.

The components of imager 10 can be implemented with, for example, the following. Mirrors 18 and 20 can be aluminum or silver coated on optical glass or metal. Mirror 18 can alternatively be a prism, and mirror 20 can alternatively be a planar mirror plate. A prism is used for mirror 20 for ease of holding the mirror in place on holder 26. Mirrors 18 and 20 can optionally be one piece of material with mirrors on both ends. Mirrors 18 and 20 are preferably positioned at 50° and 40°, respectively, from the image plane. The angles of the mirrors should total 90° for the image sensor to obtain images normal to the target, and each of the angles can thus be adjusted for desired placement in the housing. Lenses 24 can include separate lenses for each channel or be a single molded piece of material. Exemplary lens arrays are provided below. Aperture element 22 can be a multi-layer metal plate, such as BeCu base with Ni plating, with holes etched into it for the apertures 23. Holder 26 can be aluminum or a molded plastic material, and mirror 20, aperture element 22, and lenses 24 can be adhered to holder 26 or mechanically held in place on the holder. Light sources 16 can be light emitting diodes (LEDs). Cover 14 can be optical glass. Housing 12 can be metal or a plastic material. The various components of imager 10 in housing 12 can be positioned at particular distances in the optical path for a desired performance.

Figure 7:
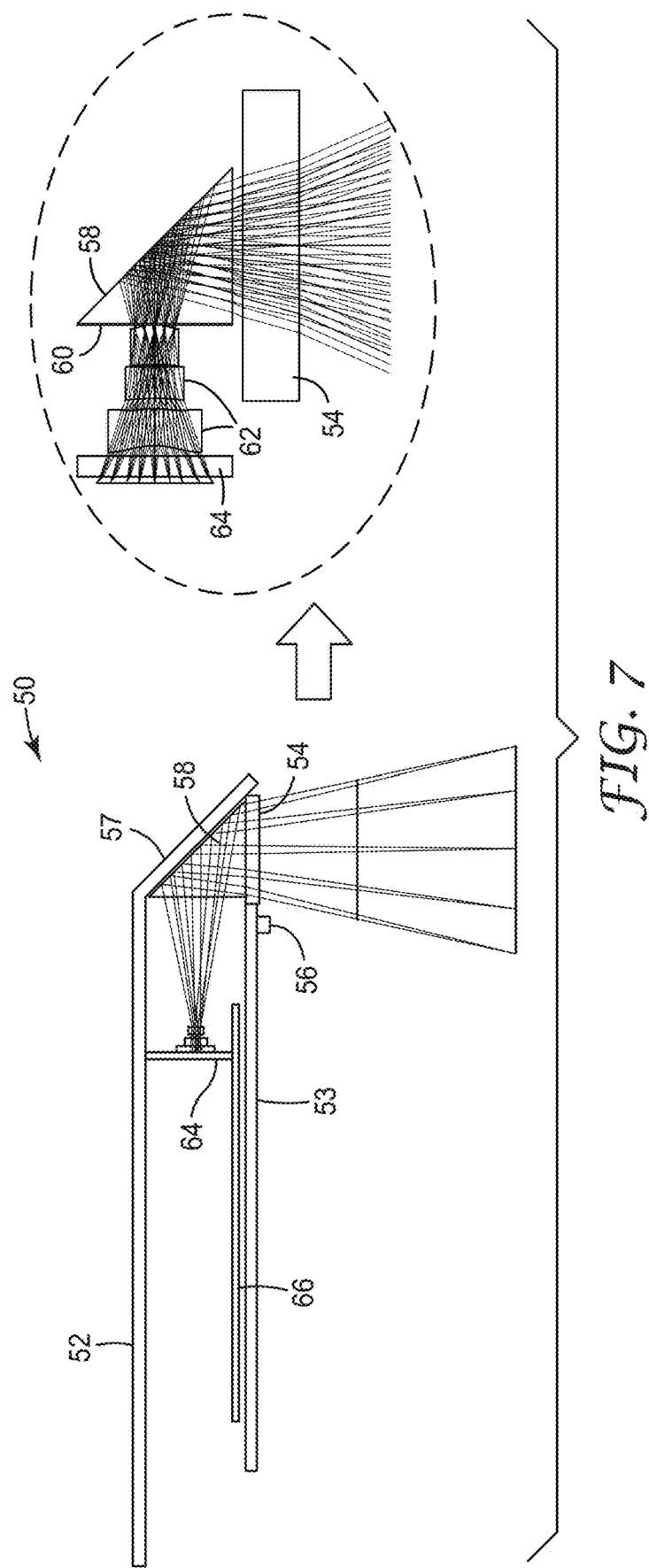
FIG. 7 is a side view of an alternative 3D imager with depth of field extension.
Figure 8:
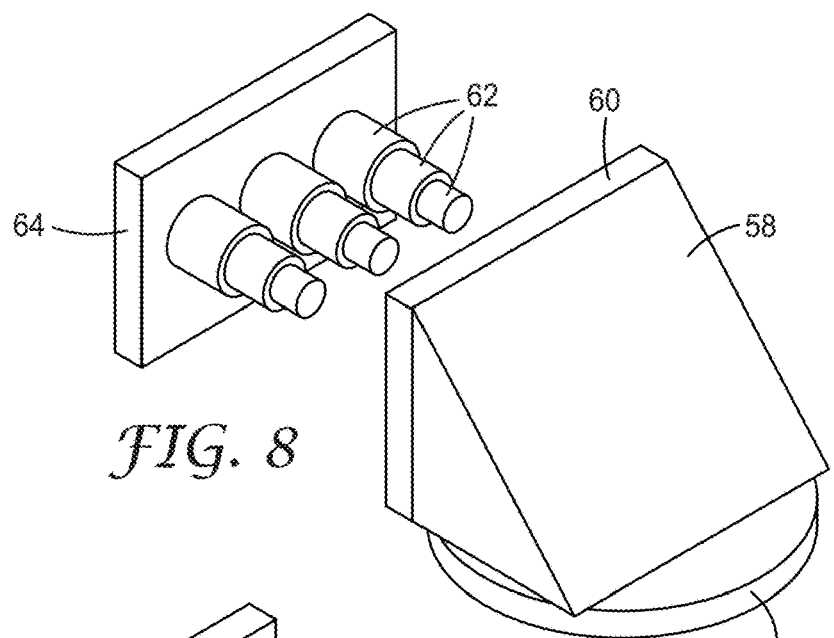
FIG. 8 is a perspective view of the 3D imager of FIG. 7.
Figure 9:
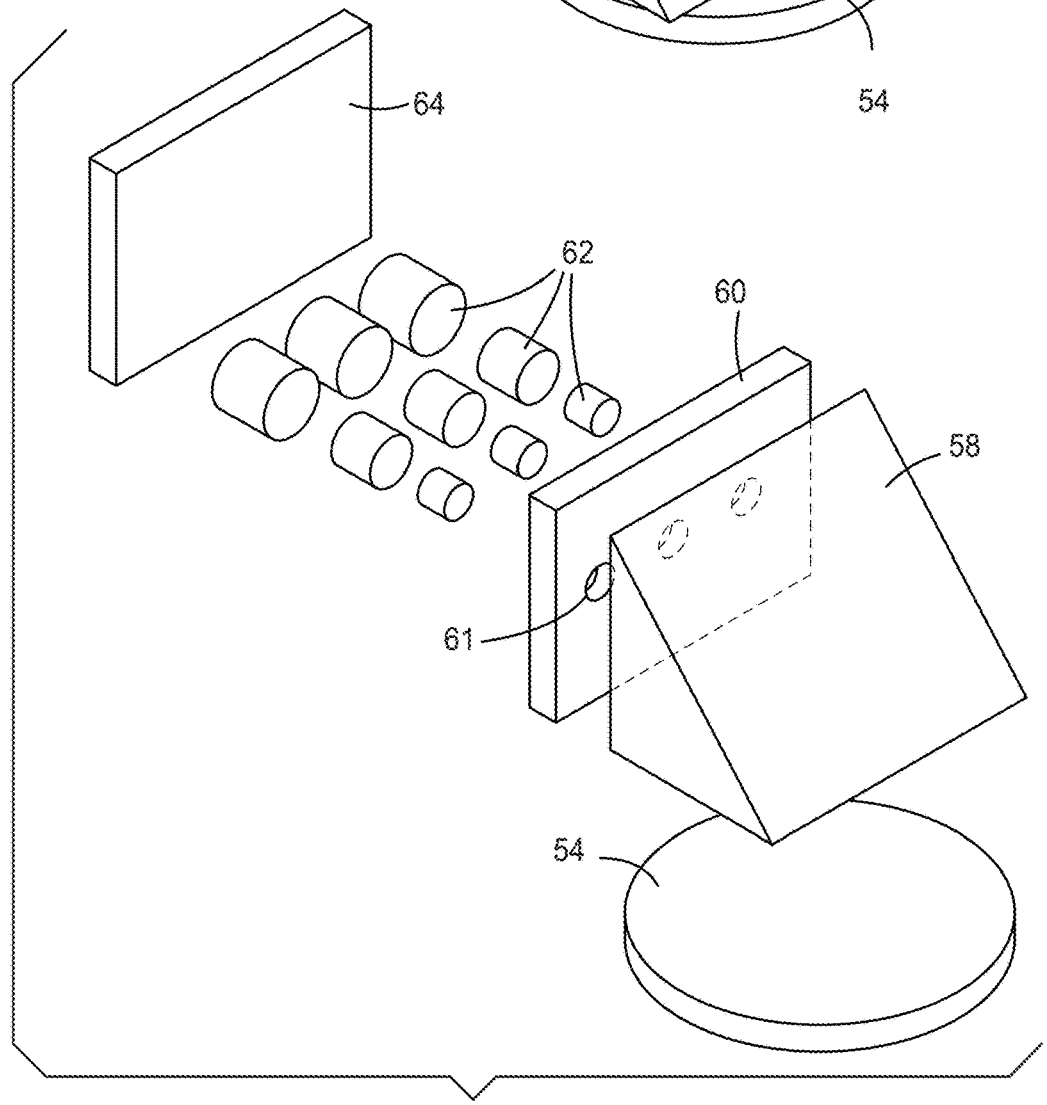
FIG. 9 is an exploded perspective view of the 3D imager of FIG. 7.

FIG. 7 is a side view of an alternative 3D imager 50 with depth of field extension using one fold mirror. FIGS. 8 and 9 are perspective and exploded perspective views, respectively, of 3D imager 50 of FIG. 7. System 50 includes a housing 52, a mirror 58, an aperture element 60, lenses 62, and an image sensor 64. Housing 52 has an angled tip 57 with mirror 58 secured adjacent an interior surface of the tip. A circuit board 66 can receive electronic signals from image sensor 64 representing the images and transmit the signals for further processing to generate a 3D model of the object.

Housing 52 includes a transparent cover 54 and light sources 56, such as LEDs, adjacent the cover to illuminate an object to be imaged. In this design, image sensor 64 is positioned substantially perpendicular to an object plane of the object. The imager has a depth of field which includes housing 52, in particular a bottom surface 53 of the housing. The depth of field can alternatively include and extend into the inside of housing 52. By having the depth of field include the housing, imager 50 can be placed directly on (in physical contact with) an object to be imaged, such as on teeth for intra-oral scanning.

FIG. 9 illustrates apertures 61 in aperture element 60 to create multiple channels. Although three apertures are shown, aperture element 60 can alternatively have two apertures for a two channel system. Aperture element 60 can be on prism mirror 58, on lenses 62, or in between mirror 58 and lenses 62 with gaps on both sides of aperture element 60. Lenses 62 can be separate lenses or one molded piece of material for each channel. The fold mirror in imager 50 can be implemented with a concave mirror or a planar mirror plate instead of the prism as shown. The components of imager 50 can be implemented with the exemplary materials provided above for imager 10.

Figure 10:
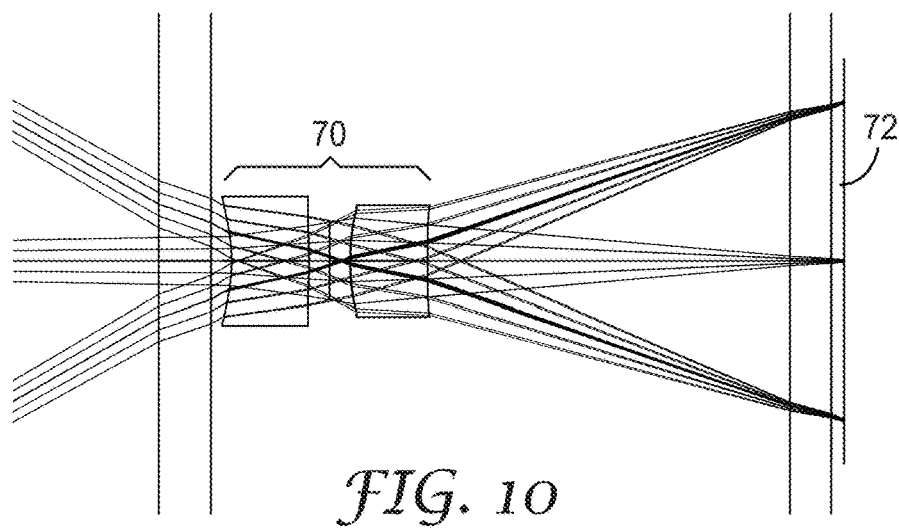
FIG. 10 is a diagram illustrating two optical elements for each optical channel in a 3D imager.
Figure 11:
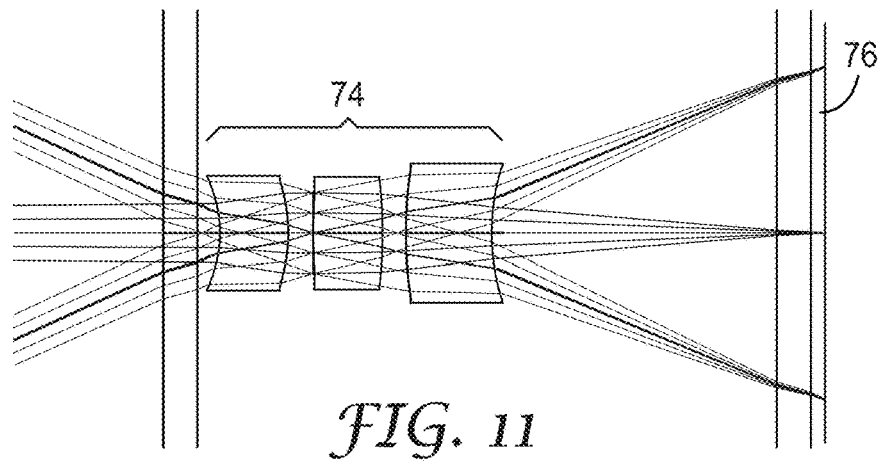
FIG. 11 is a diagram illustrating three optical elements for each optical channel in a 3D imager.
Figure 12:
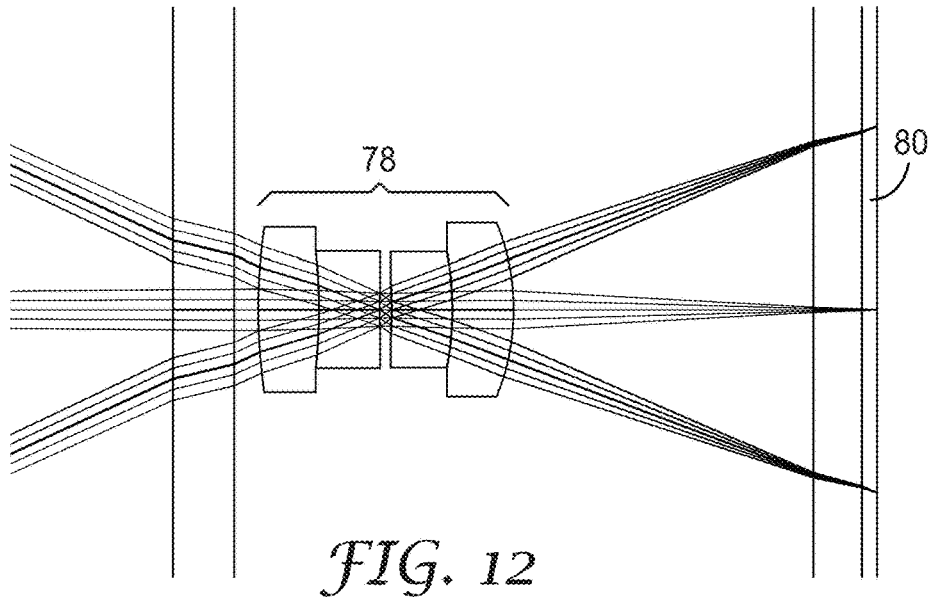
FIG. 12 is a diagram illustrating four optical elements for each optical channel in a 3D imager.

Each of the optical channels in the 3D imagers can have single or multiple optical elements. Multiple elements can achieve superior imaging quality, large depth of field, and athermalized system design. FIGS. 10-12 illustrate three options of the optics for each channel. FIG. 10 illustrates two lenses 70 positioned along an optical path normal to an image sensor 72. FIG. 11 illustrates three lenses 74 positioned along an optical path normal to an image sensor 76. FIG. 12 illustrates four lenses 78 positioned along an optical path normal to an image sensor 80.

Figure 13:
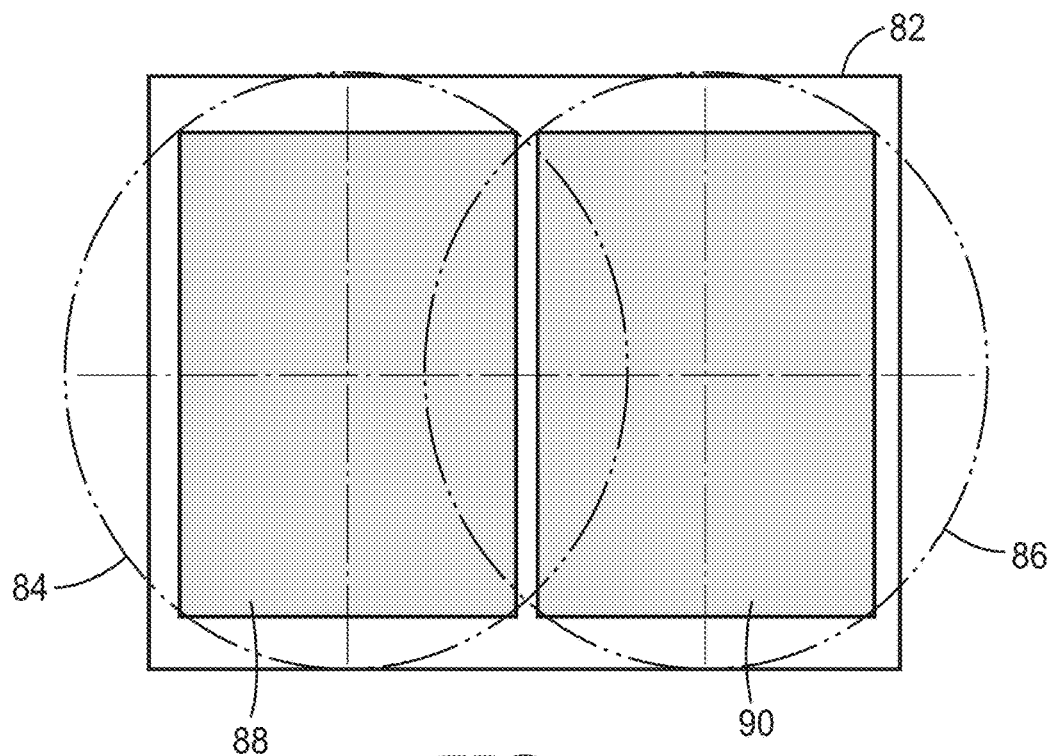
FIG. 13 is a diagram illustrating two image data regions on an image sensor in a 3D imager for obtaining multiple views in a 3D system.
Figure 14:
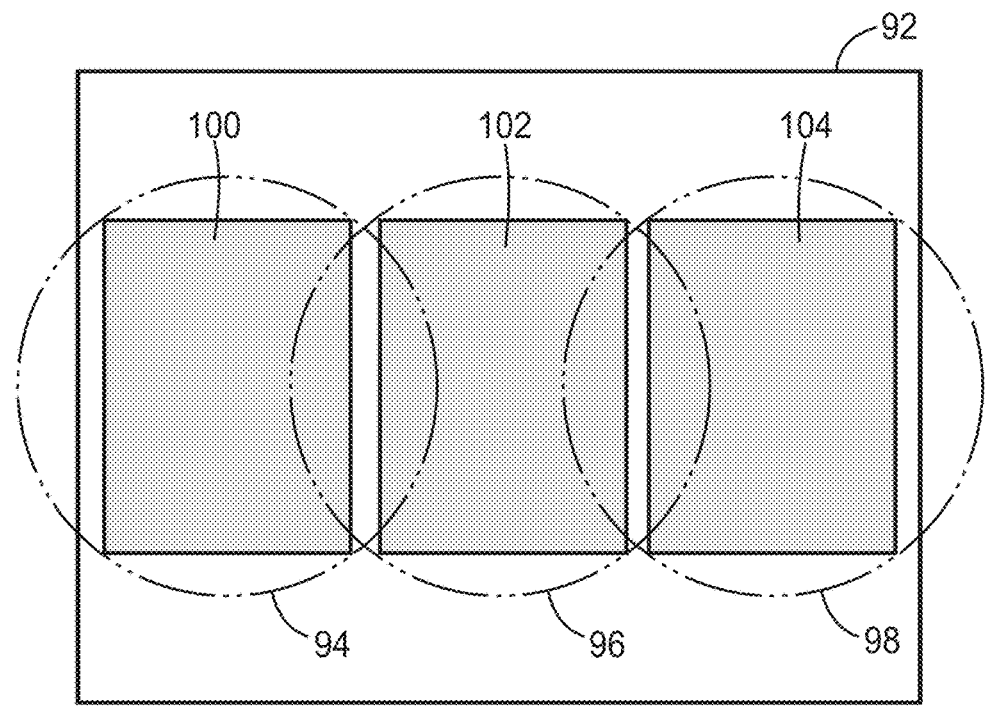
FIG. 14 is a diagram illustrating three image data regions on an image sensor in a 3D imager for obtaining multiple views in a 3D system.

The images of the object formed on the image sensor are located in two regions as shown in FIG. 13 for a two channel system or three regions as shown in FIG. 14 for a three-channel system. In FIG. 13, a first view-angle image 84 is captured in region 88 of an image sensor 82, and second view-angle image 86 is captured in region 90 of image sensor 82. In FIG. 14, a first view-angle image 94 is captured in region 100 of an image sensor 92, a second view-angle image 96 is captured in region 102 of image sensor 92, and a third view-angle image 98 is captured in region 104 of image sensor 92.

The image sensors can be implemented with, for example, any digital imager such as a CMOS or CCD sensor. The image sensor can include a single sensor, as shown, partitioned into multiple image data regions. Alternatively, the image sensor can be implemented with multiple sensors with the image data regions distributed among them.

Cover Window Fiducials

Figure 15:
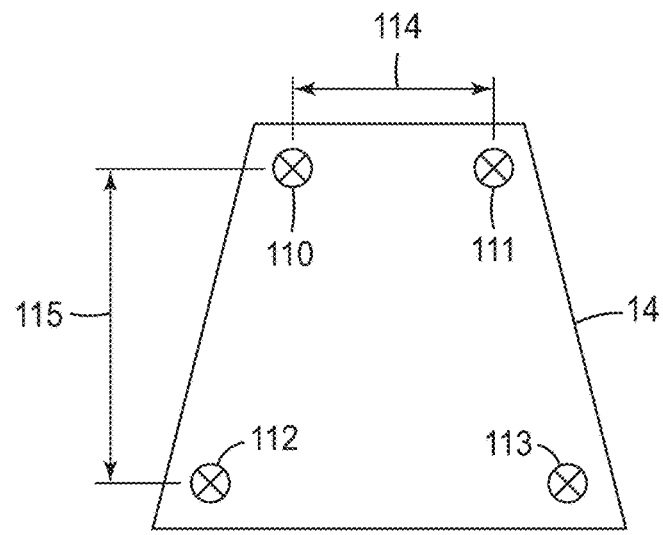
FIG. 15 is a diagram illustrating a first type of cover window fiducials for use relating to calibration.
Figure 16:
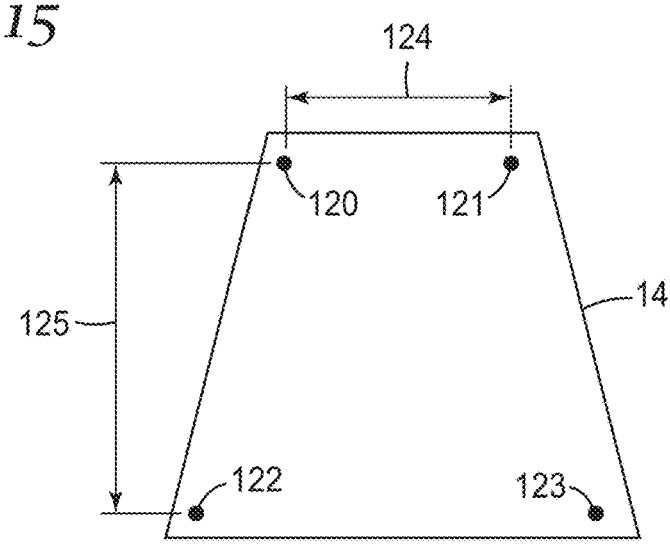
FIG. 16 is a diagram illustrating a second type of cover window fiducials for use relating to calibration.
Figure 17:
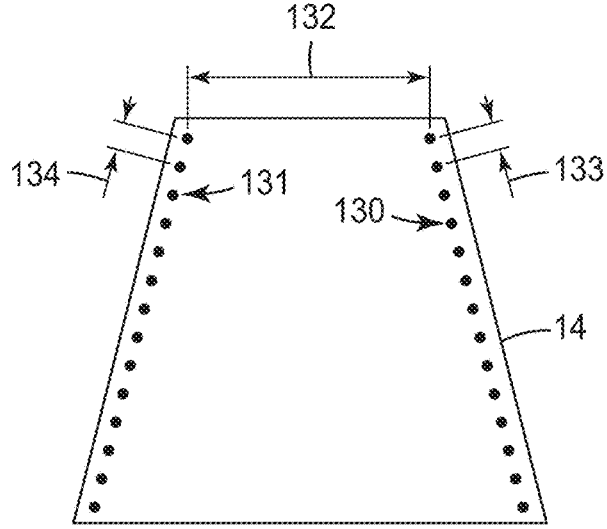
FIG. 17 is a diagram illustrating a third type of cover window fiducials for use relating to calibration.

FIGS. 15-17 are diagrams illustrating examples of cover window fiducials for use relating to calibration. FIG. 15 illustrates fiducials 110, 111, 112, and 113 located in corners of cover 14. The fiducials have a known distance between them, for example distance 114 between fiducials 110 and 111, and distance 115 between fiducials 110 and 112. These fiducials 110-113 are indicated as circles filled with an "x." FIG. 16 illustrates fiducials 120, 121, 122, and 123 located in corners of cover 14. The fiducials have a known distance between them, for example distance 124 between fiducials 120 and 121, and distance 125 between fiducials 120 and 122. These fiducials are indicated as solid dots. FIG. 17 illustrates a row of fiducials 130 on one side of cover 14 and another row of fiducials 131 on the opposing side of cover 14. The fiducials have a known distance between them, for example distance 133 between fiducials in row 130, distance 134 between fiducials in row 131, and distance 132 between the first fiducials in rows 130 and 131. These fiducials in rows 130 and 131 are indicated as solid dots.

The fiducials can be implemented with two different opaque colors. For example, the fiducials in FIG. 15 can be implemented with a first opaque color for the circle and a second opaque color, different from the first color, for the "x." As another example, the fiducials in FIGS. 16 and 17 can be implemented with a first opaque color for a portion of the solid dot and a second opaque color, different from the first color, for another portion of the solid dot. Aside from the fiducials shown in FIGS. 15-17, the fiducials can be implemented with other shapes such as, for example, triangles or squares. The fiducials are preferably located at the edges of the cover window to be outside the main view of the image sensor although still within view of and detectable by the image sensor. Alternatively, the fiducials can be located anywhere on the cover window within view of and detectable by the image sensor. Although shown on cover 14 of scanner 10, the fiducials can also be located on cover 54 of scanner 50 or on cover windows of other 3D or multi-view scanners.

By placing these fiducials as precise features on the cover window of a 3D scanner where the depth of field includes the cover window, a permanent distance-measuring standard with virtually no aging-related changes can be built into the scanner. During operation of the system, the fiducial locations can acquired and compared with the expected specifications. In particular, the distance between the fiducials as detected by the image sensor and associated system processing images from the image sensor can be compared with the actual known distance on the cover. Any discrepancy can then be used to correct errors caused by the aging or even short-term temperature related variations of the scanner. The fiducials can also be used for initial calibration of the scanner.

The cover, such as transparent glass, can provide a water-tight seal that does not interfere with imaging and permits the frequent submersion into disinfecting solution. The fiducials can include a variety of shapes and characteristics, and they should be chosen so as to minimize the likelihood of interfering with the scanning experience or calibration process. The fiducials should also be chosen to maximize the likelihood of finding their images during a typical scan. In particular, the fiducials preferably are features that the scanner can detect via the image sensor and associated processing and are not very noticeable to a user. The fiducials are preferably opaque and consequently produce a dark image of the fiducials in the video frames captured by the scanner. Since the cover lies within the depth of field of the system, the fiducials will also be in good focus. Ideally, the fiducials are located on the inner surface of the cover so as to not be exposed to the outside environment that could damage them over time. Alternatively, the fiducials can be located on the outer surface of the cover or embedded within the cover.

The distance separating the fiducials can be specified to a manufacturer, where photolithographic processes can produce the fiducials to within tolerances of ±1 micron, for example. In the case that the fiducials are placed along the corners of a 5 mm square configuration, for example, the resulting measurement standard or ground truth would have a 0.02% tolerance along the sides of the square configuration or a 0.014% tolerance along a diagonal. Such an error is more than 5 times better than the desired accuracy of the entire system for many embodiments.

By incorporating fiducials into the cover of a scanner, the user need not be an active participant in the diagnostic process. The fiducials can be a permanent feature available for measurement in almost every video frame during the intended use of the system. By being available for nearly every video frame, the fiducials afford the system a method to track the thermal-state and thus correct or augment the correction to thermal error in real time. Although the cover when implemented with glass can expand and contract due to thermal variations of the scanner, the thermal sensitivity of the scanner is due to a much larger expansion and contraction of the lens array when implemented with plastic where mere microns of movement can produce significant fractions of a percent in 3D model error. In particular, a typical glass cover has a thermal coefficient of expansion around $10^{-6}$ (per degree C.), meaning that two fiducials separated by 5 mm on room temperature glass that warms up by 20° C. would then be separated by 5.001 mm. Such a small thermal response is far smaller than the typical system can resolve. Furthermore, the cover with permanent fiducials would be stable over time and thus provide a ground truth isotropic correction for any potential long-term drifting of the scanner from the calibrated state.

The invention claimed is:

1. A 3D imaging apparatus, comprising:
a housing;
an image sensor within the housing;
a first mirror and a second mirror each within the housing, the first and second mirrors positioned to receive an image from an object external to the housing and provide the image to the image sensor; and
an aperture element having a plurality of apertures, located within the housing along an optical path between the object and the image sensor, for providing the image along a plurality of optical channels corresponding with the apertures to the image sensor; and
a transparent cover positioned within the optical path and having a plurality of fiducials detectable by the image sensor for use in calibrating the apparatus or checking a calibrated state of the apparatus, wherein the housing includes the transparent cover,
wherein a depth of field of the apparatus includes the transparent cover.

2. The 3D imaging apparatus of claim 1, wherein the image sensor is positioned substantially parallel to an object plane of the object.

3. The 3D imaging apparatus of claim 1, wherein the aperture element is located between the first and second mirrors and the image sensor.

4. The 3D imaging apparatus of claim 1, wherein at least one of the fiducials comprises a circle with an X in the circle.

5. The 3D imaging apparatus of claim 1, wherein at least one of the fiducials comprises a first opaque color and a second opaque color different from the first color.

6. The 3D imaging apparatus of claim 1, wherein at least one of the fiducials comprises an opaque dot.

7. The 3D imaging apparatus of claim 1, wherein the fiducials are located on an inside surface of the cover.

8. The 3D imaging apparatus of claim 1, further comprising a lens positioned within each of the optical channels between the aperture element and the image sensor.

9. The 3D imaging apparatus of claim 1, further comprising a light source adjacent the cover for illuminating the object.

10. The 3D imaging apparatus of claim 1, wherein the image sensor comprises a single image sensor partitioned into multiple regions corresponding with the plurality of optical channels.

11. The 3D imaging apparatus of claim 1, wherein the fiducials are located on an outer surface of the cover or embedded within the cover.

12. The 3D imaging apparatus of claim 1, wherein the cover comprises glass.

13. The 3D imaging apparatus of claim 1, wherein the apparatus is configured to detect by the image sensor a distance between the fiducials and compare the detected distance with a known distance between the fiducials on the cover.

14. A 3D imaging apparatus, comprising:
a housing;
an image sensor within the housing;
a mirror within the housing, the mirror positioned to receive an image from an object external to the housing and provide the image to the image sensor; and
an aperture element having a plurality of apertures, located within the housing along an optical path between the object and the image sensor, for providing the image along a plurality of optical channels corresponding with the apertures to the image sensor; and
a transparent cover positioned within the optical path and having a plurality of fiducials detectable by the image sensor for use in calibrating the apparatus or checking a calibrated state of the apparatus, wherein the housing includes the transparent cover,
wherein a depth of field of the apparatus includes the transparent cover.

15. The 3D imaging apparatus of claim 14, wherein the image sensor is positioned substantially perpendicular to an object plane of the object.

16. The 3D imaging apparatus of claim 14, wherein the aperture element is located between the mirror and the image sensor.

17. The 3D imaging apparatus of claim 14, wherein at least one of the fiducials comprises a circle with an X in the circle.

18. The 3D imaging apparatus of claim 14, wherein at least one of the fiducials comprises a first opaque color and a second opaque color different from the first color.

19. The 3D imaging apparatus of claim 14, wherein at least one of the fiducials comprises an opaque dot.

20. The 3D imaging apparatus of claim 14, wherein the fiducials are located on an inside surface of the cover.

21. The 3D imaging apparatus of claim 14, further comprising a lens positioned within each of the optical channels between the aperture element and the image sensor.

22. The 3D imaging apparatus of claim 14, further comprising a light source adjacent the cover for illuminating the object.

23. The 3D imaging apparatus of claim 14, wherein the image sensor comprises a single image sensor partitioned into multiple regions corresponding with the plurality of optical channels.

24. The 3D imaging apparatus of claim 14, wherein the fiducials are located on an outer surface of the cover or embedded within the cover.

25. The 3D imaging apparatus of claim 14, wherein the cover comprises glass.

26. The 3D imaging apparatus of claim 14, wherein the apparatus is configured to detect by the image sensor a distance between the fiducials and compare the detected distance with a known distance between the fiducials on the cover.

* * * * *